United States Patent [19]

Oster et al.

[11] Patent Number: 5,035,997

[45] Date of Patent: Jul. 30, 1991

[54] REDOX POLYMERIZATION DIAGNOSTIC TEST COMPOSITION AND METHOD FOR IMMUNOASSAY AND NUCLEI ACID ASSAY

[76] Inventors: Gerald Oster, 241 W. 11th St., New York, N.Y. 10014; Baruch J. Davis, Mount Sinai Medical Center, 1 Gustav Levy Pl., New York, N.Y. 10029

[21] Appl. No.: 312,525

[22] Filed: Feb. 17, 1989

[51] Int. Cl.$^5$ .................. C12Q 1/68; G01N 33/543; C08F 2/04; C08F 4/40
[52] U.S. Cl. ............................ 435/6; 435/4; 435/7.1; 435/91; 435/7.8; 436/501; 436/37; 436/538; 526/59; 526/123; 526/152; 526/171; 526/173; 526/240; 526/329.7; 526/341; 526/915; 526/918; 530/387; 935/17; 935/88; 935/78
[58] Field of Search ............... 435/4, 6, 7, 91, 7.1, 435/7.8; 436/501, 538, 37; 526/59, 123, 152, 171, 173, 240, 329.7, 341, 915, 918; 536/27; 935/17, 88, 78

[56] References Cited

U.S. PATENT DOCUMENTS

| | | | |
|---|---|---|---|
| 4,391,904 | 7/1983 | Litman et al. | 435/7 |
| 4,711,840 | 12/1987 | Nowinski et al. | 435/7 |
| 4,749,647 | 6/1988 | Thomas et al. | 435/6 |

OTHER PUBLICATIONS

Carrico, R. J., "Immunoassays Using Enzymic Cycling of Cofactor Labels", pp. 99–113; *Clinical Immunochemistry: Principles of Methods of Applications*, Eds. R. C. Boguslaski, E. T. Maggio and R. N. Nakamura (1984).
Morris, David L., "9. Apoenzyme Reactivation Immunoassays Using Flavin Adenine Dinucleotide as Label", pp. 115–130; *Clinical Immunochemistry: Principles of Methods of Applications*, Eds. R. C. Boguslaski et al. (1984).
Dainton: "Atoms and Radials in Aqueous Media", *J. Chem. Soc.*, Part 2:1533–1546, 1952.
Yang, N. L. & Oster, G., "Dye-Sensi. Photopoly. in the Presence of Rever. Oxygen Carriers", *J. of Phys. Chem.*, 74, 856 (1970).

*Primary Examiner*—Robert A. Wax
*Assistant Examiner*—Ardin H. Marschel
*Attorney, Agent, or Firm*—Sprung Horn Kramer & Woods

[57] ABSTRACT

A diagnostic test composition for detecting and measuring an analyte possessing biologic activity, the composition comprising (a) A redox catalyst system capable of converting a monomer to a polymer, the monomer capable of undergoing addition polymerization, the redox catalyst system comprising one or more chemical moieties with
  1) the analyte comprising at least one such moiety or
  2) in the case that the analyte lacks a redox catalyst property, the analyte is linked by a specific ligand to at least one such moiety or is linked by the specific ligand to a generator of at least one such moiety, and
(b) at least one monomer capable of undergoing addition polymerization.

22 Claims, No Drawings

REDOX POLYMERIZATION DIAGNOSTIC TEST COMPOSITION AND METHOD FOR IMMUNOASSAY AND NUCLEI ACID ASSAY

BACKGROUND OF THE INVENTION

1. Field of the Invention

The present invention concerns the utilization of addition polymerization, e.g., vinyl polymerization, in diagnostic test compositions for detecting and measuring an analyte possessing biologic activity and in methods for detecting and measuring an analyte possessing biologic activity.

2. Background Information

Modern diagnostic tests for trace amount of analyte possessing biologic activity, such as those encountered in clinical laboratory medicine often employ immunologic (i.e., antigen-antibody) reactions. More recently the use of probes for the assay of nucleic acids has entered the realm of clinical and research laboratories. These highly specific reactions are detected by means of a label or tag, attached to one of the components, that is either chromophoric, fluorescent, radioactive, chemiluminescent or an enzyme that can generate such signals. Chromophore labels for detection of trace analytes are of historic and academic interest only because of their low sensitivity. Color detection methods are capable of detecting no fewer than $10^{18}$ to $10^{15}$ analyte molecules per milliliter, while radioisotope detection methods can approach a detection sensitivity in the range of $10^8$ to $10^7$ analyte molecules per milliliter.

Fluorescent, chemiluminescent and enzymatic methods as characterized by relative-specific-activities can be more sensitive than radioisotope methods by at least two or more magnitudes. These are goals, however, and not achievements. Continued increases in sensitivity are reported as these methods are refined, but no magnitude jumps are anticipated.

Prior to the present invention, no one proposed the coupling of an extraneous non-catalytic substance with a catalyst component of vinyl polymerization. If the extraneous substance is a highly specific ligand for a target analyte of interest, then the production of detectable polymer can indicate the presence and site of the analyte. This linkage provides the basis of a unique detection system. The present invention when applied to analytes of biologic interest provides a diagnostic technique useful in the fields of medicine and agriculture.

SUMMARY OF THE INVENTION

It is an object of the present invention to provide a sensitive method to detect and measure analytes possessing biologic activity which method is economical and easy to use.

It is a further object of the present invention to provide a method to detect and measure such analytes in which a result can be obtained in a short amount of time.

The above objects and other objects, aims and advantages are satisfied by the present invention.

The present invention concerns a diagnostic test composition for detecting an analyte possessing biologic activity, the composition comprising (a) a redox catalyst system capable of converting a monomer to a polymer, said monomer capable of undergoing addition polymerization, the redox catalyst system comprising one or more chemical moieties with
  1. the analyte comprising at least one such moiety or
  2. in the case that the analyte lacks a redox catalyst property, the analyte is linked by a specific ligand to at least one such moiety or is linked by a specific ligand to a generator of at least one such moiety, and (b) at least one monomer capable of undergoing addition polymerization.

The present invention further concerns a diagnostic immunoassay test composition wherein the specific ligand is selected from the group consisting of an antibody, an antigen binding segment of an antibody, an antigen and a hapten, wherein when the specific ligand is an antibody or an antigen binding segment of an antibody, the analyte is an antigen or a hapten and wherein when the specific ligand is an antigen or hapten, the analyte is an antibody or an antigen binding segment of an antibody.

The present invention further concerns a diagnostic test composition for the assay of a nucleic acid wherein the specific ligand is a hybridizable nucleic acid probe containing a known sequence, the sequence being single stranded and complementary to a single stranded segment of a nucleic acid analyte.

The present invention is further directed to a method for detecting an analyte that is an oxidant or an enzyme that generates an oxidant comprising (a) combining 1) the oxidant analyte or 2) the enzyme analyte that generates an oxidant from its precursor, the oxidant in the presence of a reductant capable of converting a monomer to a polymer through addition polymerization, the monomer capable of undergoing addition polymerization, 3) a reductant and 4) in the case of the enzyme analyte, a precursor of the oxidant, together with at least one monomer capable of undergoing addition polymerization, and (b) determining the extent of addition polymerization as an indicator of the presence and/or quantity of analyte.

The present invention is further directed to a method for detecting an analyte that is a reductant or an enzyme that generates a reductant comprising (a) combining 1) a reductant analyte or 2) an enzyme analyte that generates a reductant from its precursor, the reductant in the presence of an oxidant capable of converting a monomer to a polymer through addition polymerization, the monomer capable of undergoing addition polymerization, 3) an oxidant and 4) in the case of the enzyme analyte, a precursor of a reductant, together with at least one monomer capable of undergoing addition polymerization, and (b) determining the extent of addition polymerization as an indicator of the presence and/or quantity of analyte.

The present invention is further directed to a method for detecting an antibody or an antigen binding segment of an antibody comprising (a) linking an antigen or a hapten to 1) an oxidant or 2) to an enzyme that generates from a precursor an oxidant of a redox catalyst system for addition polymerization of a reactive vinyl monomer or a vinylidine monomer, (b) contacting the linked antigen or hapten with a complementary antibody or an antigen binding segment of an antibody in the presence of a reductant of the redox catalyst system, and in the case of the enzyme, the precursor of the oxidant, and with at least one monomer capable of undergoing addition polymerization, and (c) determining the extent of addition polymerization as an indicator of the presence and/or the quantity of the antibody or an antigen binding segment of an antibody.

The present invention is still further directed to a method for detecting an antigen or a hapten comprising (a) linking an antibody or an antigen binding segment of antibody to 1) an oxidant or 2) to an enzyme that generates from a precursor an oxidant of a redox catalyst system for addition polymerization of a reactive vinyl monomer or a vinylidine monomer, (b) contacting the linked antibody or an antigen binding segment of antibody with a complementary antigen or hapten in the presence of a reductant of the redox catalyst system, and in the case of the enzyme, the precursor of the oxidant and with at least one monomer capable of undergoing addition polymerization, and (c) determining the extent of addition polymerization as an indicator of the presence and/or the quantity of the antigen or hapten.

The present invention is further directed to a method for detecting an antibody or an antigen binding segment of an antibody comprising (a) linking an antigen or a hapten to 1) a reductant or 2) an enzyme that generates from a precursor a reductant, the reductant being an element of a redox catalyst system for addition polymerization of a reactive vinyl monomer or a vinylidine monomer, (b) contacting the linked antigen or hapten with a complementary antibody or an antigen binding segment of antibody in the presence of an oxidant of the redox catalyst system and in the case of the enzyme, a precursor of the reductant, together with at least one monomer capable of undergoing addition polymerization, and (c) determining the extent of addition polymerization as an indicator of the presence and/or the quantity of the antibody or an antigen binding segment of an antibody.

The present invention is still further directed to a method for detecting an antigen or hapten comprising (a) linking an antibody or an antigen binding segment of an antibody to 1) a reductant or 2) an enzyme that generates from a precursor a reductant, the reductant being an element of a redox catalyst system for addition polymerization of a reactive vinyl monomer or a vinylidine monomer, (b) contacting the linked antibody or an antigen binding segment of an antibody with a complementary antigen or hapten in the presence of an oxidant of the redox catalyst system and in the case of the enzyme, a precursor of the reductant together with at least one monomer capable of undergoing addition polymerization, and (c) determining the extent of addition polymerization as an indicator of the presence and/or the quantity of the antigen or hapten.

The present invention is further directed to a method for detecting a nucleic acid comprising (a) linking a hybridizable nucleic acid probe containing a known sequence, the sequence being single stranded and complementary to a single stranded segment of an analyte nucleic acid to a 1) an oxidant or 2) an enzyme that generates an oxidant from its precursor, the oxidant in the presence of a reductant capable of converting a monomer to a polymer through addition polymerization, the monomer capable of undergoing addition polymerization, (b) contacting the linked nucleic acid probe with the analyte nucleic acid in the presence of a reductant and in the case of the enzyme, a precursor of the oxidant, together with at least one monomer capable of undergoing addition polymerization, and (c) determining the extent of addition polymerization as an indicator of the presence and/or the quantity of nucleic acid analyte.

The present invention is still further directed to a method for detecting a nucleic acid comprising (a) linking a hybridizable nucleic acid probe containing a known sequence, the sequence being single stranded and complementary to a single stranded segment of an analyte nucleic acid to 1) a reductant or 2) an enzyme that generates a reductant from its precursor, the reductant in the presence of an oxidant capable of converting a monomer to a polymer through addition polymerization, the monomer capable of undergoing addition polymerization, (b) contacting the linked nucleic acid probe with the analyte nucleic acid in the presence of an oxidant and in the case of the enzyme, a precursor of the reductant together with at least one monomer capable of undergoing addition polymerization, and (c) determining the extent of addition polymerization as an indicator of the presence and/or quantity of nucleic acid analyte.

The present invention is further directed to a method for detecting a nucleic acid comprising (a) contacting a hybridizable nucleic acid probe containing a known sequence, the sequence being single stranded and complementary to a single stranded segment of a nucleic acid analyte, with the analyte, (b) linking the probe to 1) an oxidant or 2) an enzyme that generates an oxidant from its precursor, the oxidant in the presence of a reductant capable of converting a monomer to a polymer through addition polymerization, the monomer capable of undergoing addition polymerization, in the presence of a reductant and in the case of an enzyme, a precursor of an oxidant, together with at least one monomer capable of undergoing addition polymerization, and (c) determining the extent of addition polymerization as an indicator of the presence and/or the quantity of nucleic acid analyte.

The present invention is further directed to a method for detecting a nucleic acid analyte comprising (a) contacting a hybridizable nucleic acid probe containing a known sequence, the sequence being single stranded and complementary to a single stranded segment of a nucleic acid analyte, with the analyte, (b) linking the probe to 1) a reductant or 2) an enzyme that generates a reductant from its precursor, the reductant in the presence of an oxidant capable of converting a monomer to a polymer through addition polymerization, the monomer capable of undergoing addition polymerization, in the presence of an oxidant and in the case of an enzyme, a precursor of a reductant, together with at least one monomer capable of undergoing addition polymerization, and (c) determining the extent of addition polymerization as an indicator of the presence and/or quantity of nucleic acid analyte.

In contrast to the aforesaid heretofore employed efforts to refine well-established methods, the present invention provides additional amplification factors inherent in the catalytic and chain reaction nature of addition polymerization. The potential sensitivity is exceedingly high for the following reasons:

(1) The oxidant and/or the reductant can be generated by an enzyme-labeled analyte. Horseradish peroxidase is one such enzyme.

(2) A single initiating molecule can initiate the formation of a polymer chain molecule composed of $10^5$ to $10^6$ monomer molecule units. A particle visible to the naked eye under light scattering conditions can be the product of as few as 2 to 4 initiating molecules.

The present invention is applicable to virtually all immunoassay techniques and nucleic acid hybridization techniques and thereby renders such techniques considerably more sensitive and convenient than the conventional techniques discussed hereinabove. The present invention is directly applicable to enzyme linked assays including the well established peroxidase assays. Horse radish peroxidase, with its known high turnover rate (5 million hydrogen peroxide molecules converted per enzyme molecule per minute), can by the present invention catalyze addition polymerization.

DETAILED DESCRIPTION OF THE INVENTION

The present invention concerns a diagnostic test which comprises a chemical composition which contains one or more test substances linked through a specific ligand to a target analyte of biologic interest. The composition in the presence of the analyte undergoes addition polymerization e.g., vinyl polymerization, to yield a measurable amount of polymer. More specifically, the composition contains (a) a redox catalyst system designed to convert monomer to polymer and (b) one or more monomers, e.g., vinyl monomers or vinylidine monomers, capable of undergoing addition polymerization.

Analytes according to the invention are comprised of the following two classes:

(a) the analyte possesses a redox catalyst moiety property, that is, it is an oxidant or a generator of an oxidant or it is a reductant or a generator of a reductant;

(b) the analyte lacks redox catalyst properties but is capable of forming a stable complex with a specific ligand that is capable of being linked to a redox catalyst moiety or to a generator (enzyme) of such a moiety.

The class of analytes possessing redox catalyst properties or capable of generating such moieties is comparatively small, but includes members of considerable biologic interest. Reduced nicotinamide adenine dinucleotide (NADH) and reduced nicotinamide adenine dinucleotide diphosphate (NADPH), ascorbic acid, among others, are capable of participating in a redox reaction and are therefore detectable. AND and NADP oxidoreductase enzymes can generate reduced NADH and NADPH.

The second class of analytes, those lacking redox catalyst properties, but capable of forming stable complexes with their specific ligands, is a very numerous class comprised of two large groups, namely immunoreactive analytes and nucleic acid analytes, and smaller groups such as lectins, messengers, specific cell surface receptors, gene regulating proteins, haptoglobins, etc.

In the present invention an analyte, e.g., an antibody analyte, an antigen analyte or a hapten analyte is linked to one or more chemical moieties of the redox catalyst system. As noted above, the specific ligand and its target analyte are the elements that combine to form the immune complex common to all immunoassay procedures. These include the immunoglobulin antibodies, antibody segments that contain the complementary site, antigens and haptens. As is also evident either element of the complex can serve as the specific ligand for the detection of the other, the analyte.

In the case of a nucleic acid assay by means of a hybridizable probe, the analyte is deoxyribose nucleic acid (DNA), ribose nucleic acid (RNA) or a polynucleotide segment of a nucleic acid whose complementary portion for hybridization is in a single stranded state.

Since with few exceptions the specific ligands for assay of immunoreactive substances and nucleic acids do not possess redox catalytic properties, the ligand, either before or after it has formed its specific complex with the target analyte, must be bound to a moiety or a generator of a moiety of the redox catalyst system. The types of linkages and intermediate linking molecules are well known in the art and are applicable to both immunoassay and nucleic acid assay.

That is, by means of one or more linker molecules, the target analyte can be linked through its specific ligand to a moiety of the catalyst system. For example, if a drug can be rendered immunogenic, the antibody that it evokes serves as the specific ligand that provides the necessary linkage; by coupling a generator (an enzyme) of an oxidant, a reductant or a generator (an enzyme) of a reductant to the antibody, a reagent is formed which binds specifically to the drug and initiates polymer formation. Multiple combinations of intermediate linkages as presently utilized in immuno-diagnostic techniques are equally applicable to the present invention. Thus, glucose oxidase enzyme can be coupled to avidin and the antigen of an antibody coupled to biotin so that in this particular linkage system the enzyme is the generator of a oxidant and the antibody is the analyte. Here the enzyme is linked to the antibody (or to the nucleic acid) through a biotin-avidin complex which once formed is essentially non-dissociable. Alternative linkages through antibodies to avidin, antibodies to biotin, and through Protein A can, for example, be utilized.

Further sensitivity can be gained by linking multiple catalyst moieties to a natural or synthetic polymer, which in turn is bonded to the specific ligand. If the molecule carrying the catalyst moieties is such a polymer or is an enzyme, its bulkiness may impede the complexation of the ligand with the analyte. This problem can be obviated by first complexing the ligand with the analyte, then linking the ligand to the catalyst system moiety.

In the present invention on causing the polymerization to occur, the polymer is thereby produced at the site of the analyte. In general, wherever in a biological specimen a catalyst moiety is bound (covalently or otherwise), then by the present invention the polymer will be produced at that site. Further, the present invention is applicable at the microscopic level permitting the detection and localization of the analyte at the histochemical and cytochemical levels (e.g., tissue sections, individual cells and microorganisms).

In the present invention a redox catalyst system generates initiating molecules that initiate the polymerization process. The catalyst system includes an oxidant, an electron acceptor, a reductant (which reacts with the electron acceptor), an electron donor to yield initiating molecules to initiate addition polymerization of a vinyl monomer or vinylidine monomer.

In common with photocatalyst systems and in contrast to those of thermal polymerization, the redox catalyst system serves as a highly efficient source of initiating molecules at temperatures that protect against thermal denaturation of sensitive biological substances. Redox catalysis is also characterized by high yields of polymer, high yields of high molecular weight polymer and by a reduced induction time.

The bulk of the delay in onset of polymerization is consequent to the presence of oxygen, which by competing with monomers for initiator radicals or by combining with growing polymer chains, delays the onset of polymerization and reduces chain length. In instances in which a catalyst component is present in trace quantities, even small amounts of oxygen can significantly alter the onset and course of polymerization.

In the present invention when the ligand-analyte is linked to the oxidant moiety of the redox catalyst system, the source of the oxidant is typically an oxidase enzyme that generates hydrogen peroxide. The hydrogen peroxide can be used in two different detection methods. In the first, the hydrogen peroxide serves directly as the oxidant and in combination with an appropriate reductant can be decomposed to hydroxyl radical which initiates polymerization. In the second, the hydrogen peroxide can serve as oxidant for a peroxidase enzyme, which in the presence of a appropriate substrate can generate free radicals that initiate polymerization. It is noted that previous attempts to utilize peroxidase enzyme as a source of free radicals for the initiation of vinyl polymerization failed (F. Dainton, *J. Chem. Soc.*, 1533, (1952)). One discovery of the present invention is the demonstration that of the large group of donors that can serve as donor substrates for peroxidase, only a very limited class of them can yield free radicals capable of initiating polymerization.

Alternative catalyst systems employing ionic mechanisms for addition polymerization are also applicable in this invention.

In the present invention the oxidases that generate hydrogen peroxide include (non-limiting) the following: lactate oxidase, glucose oxidase, L-gulonolactone oxidase, galactose oxidase, L-2-hydroxyacid oxidase, aldehyde oxidase, xanthine oxidase, dihydroorotate dehydrogenase (oxygen oxidoreductase), D-aspartate oxidase, L-amino acid oxidase, D-amino acid oxidase, monamine oxidase, pyrodoxaminephosphate oxidase, diamine oxidase, sarcosine oxidase, spermine oxidase, sulfite oxidase, hexose oxidase, L-sorbose oxidase, pyridoxol-4-oxidase, alcohol oxidase, tyramine oxidase, putrescine oxidase, 6-hydroxy-L-nicotine oxidase, 6-hydroxy-D-nicotine oxidase, 2-aminophenol oxidase, superoxide dismutase and cytochrome oxidase.

In the present invention non-limiting examples of reductants for the decomposition of hydrogen peroxide to hydroxyl radical include the following: ascorbic acid, allylthiourea, dithioerythritol and bisulfite. Also included are combinations of ferric ion, e.g., as an EDTA chelate, with one or more auxillary reductants such as acetylacetone, acetylacetone with a tertiary amine, ascorbic acid, dithioerythritol, superoxide and dihydroxy phenylalanine (DOPA).

In the present invention when the analyte, through its specific ligand, is linked to the reductant portion of the catalyst moiety, several different detection systems can be employed. Examples of these detection systems are as follows:

1. Linkage can be made to a metal chelate, e.g., iron ethylenediaminetetraacetic acid (EDTA), in a composition that also contains hydrogen peroxide and a second reductant, such as dihydroxyphenylalanine (DOPA). Iron in its reduced form provides reductant for the peroxide. The iron is cycled back to its reduced state by the second reductant, DOPA, which in the absence of iron is unable to convert the peroxide to hydroxyl radical.
2. Linkage can be made to an enzyme, e.g., xanthine oxidase or a dehydrogenase such as glutathione reductase and ferredoxin nicotinamide adenine phosphate reductase, that generates superoxide. In a composition that also contains iron and hydrogen peroxide, the superoxide by reducing iron provides a reductant for the peroxide.
3. Linkage can be made to a peroxidase enzyme in a composition that also contains hydrogen peroxide and one of the limited class of peroxidase substrates that yields initiator radicals.

In those instances when the ligand-analyte is linked to the reductant moiety of the catalyst system, the oxidant is selected from the group consisting of hydrogen peroxide and water soluble peroxy derivatives.

In the present invention non-limiting examples of peroxidase enzymes include the following: horseradish peroxidase, thyroid peroxidase, salivary peroxidase, intestinal peroxidase, lactoperoxidase and microperoxidase.

In the present invention non-limiting examples of substrates for peroxidase enzyme include acetylacetone, dihydroxyfumaric acid and nicotinamide adenine dinucleotide phosphate (reduced).

Addition polymerization of vinyl monomers is a chain reaction whereby a single initiator molecule may cause the consecutive conversion of thousands, or even millions, of monomer units to form a high molecular weight polymer molecule. Although the process of polymerization of vinyl monomers is widely practiced in industry to yield such useful plastics as polystyrene, polymethyl methacrylate, polyacrylonitrile, and the like, the process has not heretofore been used as an indicator of trace amounts of biologic substances. Aside from the sensitivity of the reaction, its result is readily observed and easily measured. High molecular weight polymers are characterized by the fact that their physical properties are markedly different from those of the parent monomer. Thus acrylamide, for example, is soluble in methanol, but polyacrylamide is insoluble in methanol; acrylonitrile is water soluble (to the extent of 7 percent), but polyacrylonitrile is water insoluble; calcium acrylate is soluble in water, but polycalcium acrylate being a highly crosslinked polymer forms a second phase in water and so on. Thus these polymers are recognized in an appropriate solvent by the white light scattering mass which they form when polymerization of the monomer ensues. Many high polymers even in solvents which do not precipitate the polymer differ from the parent monomer in that they are tacky or sticky, whereas the monomer is not. Thus aqueous solutions of such polymers as polyacrylamide and polymethacrylic acid form sticky highly viscous, colorless solutions which can plug up porous sieves, whereas the aqueous solutions of the monomer are non viscous. Thus the production of even a small quantity of high polymer is readily observable and measurable.

The following monomers among others can be employed singularly or in combination in the present invention: acrylamide, N-octyl acrylamide, methacrylamide, N-methyl-acrylamide, acrylic acid, methacrylic acid, hydroxymethyl acrylamide, methylene bisacrylamide, acrylonitrile, methyl acrylate (and higher esters), ethylene glycol methacrylate, propylene glycol methacrylate, acrylamido propane sulfonic acid, vinyl pyrrolidone, vinyl pyridine, and the multivalent salts of acrylic and methacrylic acids, including calcium, barium, strontium, cadmium, neodymium, uranium and europium. Still further, preformed, synthetic and natural polymers to which vinyl groups can be coupled and which are capable of forming addition polymers can be used.

The intended method of detection of the polymer would usually be determined from the choice of the monomer. The most obviously visible polymer is that where dense crosslinks are produced, that is, where the monomer is multi-functional, e.g. difunctional. Methylene bisacrylamide is one such monomer. The most versatile monomers are the divalent metal salts of acrylic acid. Many of the very sensitive systems of the present invention use calcium or barium acrylate. Barium acrylate might be effective for electron microscopy. Not only would the resolution be high because the polymer would remain restricted to the site of the analyte but also the polymer is relatively dense toward the penetration of electrons. Hence very thin samples of only a few Angstroms should show high contrast. Even more effective is uranium acrylate. Uranium (II) salts are fluorescent so the polymer would fluoresce under the action of near ultraviolet light. The fluorescence would be particularly intense because each monomer unit of the polymer is fluorescent. A more effective fluorescent monomer is europium (II) acrylate. Here the europium polyacrylate can be further processed to yield another europium chelate which emits red light (maximum 615 nm) when excited by 365 nm radiation. Red fluorescence can be measured with high precision in biological specimens because the background fluorescence is negligible.

There are a number of auxiliary techniques which further enhance the sensitivity and convenience of the present invention. For example, if the monomer is acrylamide the resultant polymer is sticky and will trap or entrain pigment granules thereby acquiring a color of high tinctorial power.

Other types of granules which enhance the detection of the polymer include reflecting metals, e.g., aluminium powder, phosphorescent pigments (e.g., doped cadmium sulfide) or magnetic pigments for magnetic readout. Still further, soluble or particulate reagents entrained in the growing polymer or trapped on the surface of the polymer can serve as initiators of a second stage cascade that can, for example, generate additional polymer or a dye product.

Aggulutination of a suspension of latex particles can be a very sensitive measure of vinyl polymerization. The polymer, unlike the monomer, could adhere to the latex particle causing a clumping of the particles.

The sensitivity and rapidity of detection of immunological reactions and nucleic acid hybridization using the present invention make practicable the efficient and economical search for the quantitation of possible interactions of a given test species with a very large number of substrates or complimentary species. The present invention provides a means of performing automatic rapid screening of very large arrays of substances as is desired for analysis of gene compositions. Such arrays might include arrays of nucleic acids and their subunits and proteins and their subunits as encountered in the universe of immune phenomena or of nucleic acid hybridization.

As noted earlier, oxygen is a free radical scavenger that, at least when present in excess, can retard and inhibit polymerization. To counteract these effects, flushing of the system with nitrogen gas can be performed to at least transiently approach optimum conditions. Simple and economic industrial control of oxygen concentration has never been achieved. However, N. L. Yang and G. Oster, *J. Physical Chem.*, 74, 856 (1970) described an effective method for aqueous systems comprising cobalt chelates which buffer oxygen. In the present invention an additional method has been found which employs enzymes that chemically reduce dissolved oxygen to superoxide, hydrogen peroxide or water.

Cobalt chelates such as those (non-limiting) of glycylglycine, histidine, diethylene triamine, triethylene tetramine and vitamin $B_{12a}$ are suitable in the alkaline range. All of the oxygen oxidoreductases, including the preceding list of oxidases that generate peroxide, are suitable in the neutral pH range.

The examples given below are representative of the present invention and are not meant to limit the invention.

EXAMPLE 1

In this example the ligand is linked to an enzyme that generates hydrogen peroxide. Hydrogen peroxide in the presence of ascorbic acid, a reductant, yields free radicals capable of initiating vinyl polymerization.

A. Glucose oxidase enzyme is coupled to antibody and this conjugate is allowed to combine with its antigen, which is spotted and fixed on a glass slide. The uncombined conjugate is washed off. The glass slide is dipped into a solution containing 10% calcium acrylate, 5% glucose and 0.5% ascorbic acid for 10 minutes. At the end of this time a grossly visible white precipitate is present at the site of the antigen.

B. The above example A is repeated with a glucose oxidase-albumin conjugate in place of the glucose oxidase antibody conjugate. No white precipitate is visible on the glass slide.

C. The above example A is repeated without the introduction of enzyme conjugate. No white precipitate is visible on the glass slide.

D. The above example A is repeated by using uranyl acrylate in place of calcium acrylate and the amount of antigen used is one-thousandth of that above. Following incubation no polymer is grossly visible, but on examination with a mineralogist's (Woods, 365 nm) lamp a fluorescent polymer is seen at the site of the antigen.

EXAMPLE 2

The xanthine oxidase reduction of oxygen to hydrogen peroxide (in the presence of xanthine) generates an intermediate capable of reducing ferric to ferrous. The latter ion serves as a reductant in a hydrogen peroxide redox system for vinyl polymerization.

Xanthine oxidase enzyme is coupled to antigen and this conjugate is allowed to combine with its antibody which is spotted and fixed on a glass slide. The uncombined conjugate is washed off. The glass slide is dipped into a solution saturated with xanthine, 2% methylene bisacrylamide, 0.2% ferric EDTA for 10 minutes. At the end of this time a grossly visible white precipitate of polymethylene bisacrylamide is visible at the site of the antibody.

EXAMPLE 3

In this example, in contrast to Example 2, the iron chelate, rather than the enzyme, is conjugated to the ligand for the analyte.

An antigen is reacted with the anhydride of EDTA and the conjugate is treated with an iron salt to form ferric chelate. This product is allowed to combine with an antibody which is spotted and fixed on a glass slide. Uncombined antigen-iron chelate is washed off. The slide is dipped into a solution saturated with xanthine and containing 2% methylene bisacrylamide and 0.001% xanthine oxidase for 10 minutes. At this time a grossly visible precipitate of polymer can be seen at the site of the antigen.

EXAMPLE 4

In this example horseradish peroxidase using hydrogen peroxide as oxidant converts dihydroxyfumaric acid to free radicals that initiate vinyl polymerization.
  A. Horseradish peroxidase enzyme is conjugated to antigen and the conjugate is allowed to combine with its antibody, which has been adsorbed onto the walls of a polystyrene well. Uncombined conjugate is washed out. To the well is added 0.03% hydrogen peroxide and 0.02% dihydroxyfumaric acid along with 15% calcium acrylate and the solution is allowed to stand for 5 minutes. At the end of the time the well is emptied of solution and washed out revealing the antibody coated surface to be covered with a white precipitate of polycalcium acrylate.
  B. Example 4A is repeated, but with 0.5% acetylacetone in place of dihydroxyfumaric acid. The result is the same.
  C. Example 4A is repeated, but with NADPH in place of dihydroxyfumaric acid. The result is the same.

EXAMPLE 5

Morris ("Apoenzyme Reactivation Immunoassays Using Flavin Adenine Dinucleotide as Label", *Clinical Immunochemistry: Principles of Methods and Applications,* Eds. R. C. Boguslaski, E. T. Maggio and R. M. Nakamura, pp. 115-130, (1984), Little Brown and Company, Boston/Toronto) developed a homogeneous immunoassay based on the following data. Glucose oxidase enzyme is a flavoprotein that can be decomposed under non physiologic conditions to flavin (flavin adenine dinucleotide, FAD) which is the prosthetic group or coenzyme and the protein portion or apoenzyme. The separated component are inactive, but under physiological conditions reassociate forming the fully active enzyme; furthermore, that when the prosthetic group (FAD) is covalently bonded to another chemical species, for example, an antigen or hapten, the enzyme-antigen conjugate is usually active, but the enzyme-antigen-antibody complex is usually inactive.

From the above, a test can be devised, a homogeneous assay, in which an analyte antigen (analyte hapten) competes with the enzyme-antigen (or enzyme-hapten) for a small amount of antibody, leaving a portion of the enzyme-antigen (or enzyme-hapten) free of antibody and therefore enzymatically active. The concentration of active enzyme is thus proportional to the amount of test analyte antigen (or hapten). Procedure: A known amount of analyte-FAD conjugate is mixed with test analyte and glucose oxidase apoenzyme is added in excess to form analyte FAD-apoenzyme (analyte-enzyme). Next a small measured amount of antibody is added and the solution gently agitated for 10 minutes. Following this, 5% glucose, 10% barium acrylate and 0.5% ascorbic acid are added and the solution allowed to stand for an additional 10 minutes. The solution becomes increasingly turbid in this interval at a rate proportional to the concentration of the analyte.

EXAMPLE 6

A. A biotinylated nucleic acid probe is allowed to hybridize with its complementary single stranded deoxyribose nucleic acid (DNA) which is first transferred to and immobilized on nitrocellulose paper. Following hybridization the uncombined probe is removed. The nitrocellulose paper is then soaked in bovine albumin to block non-specific adsorption. Next the nitrocellulose paper is immersed in a solution containing horseradish peroxidase coupled avidin. Following washout of uncombined avidin the nitrocellulose paper is immersed in a solution containing 0.03% hydrogen peroxide, 0.02% dihydroxyfumaric acid along with 20% acrylamide and 0.5% methylene bisacrylamide and the solution is allowed to stand for 5 minutes. The nitrocellulose paper is dusted with carbon black powder and then shaken to remove non adhering carbon black particles. Hybridization sites are visible as black spots.

B. Example 6A is repeated, but with 0.5% acetylacetone in place of dihydroxyfumaric acid. The result is the same.

C. Example 6A is repeated but with NADPH in place of dihydroxyfumaric acid. The result is the same.

It will be appreciated that the instant specification and examples are set forth by way of illustration and not limitation, and that various modifications and changes may be made without departing from the spirit and scope of the present invention.

What is claimed is:

1. A diagnostic test composition for detecting and measuring an analyte possessing biologic activity, the composition comprising
    (a) a redox catalyst system capable of converting a monomer to a polymer, said redox catalyst system operating by free radical initiation, the redox catalyst system comprising one or more chemical moieties and 1) said analyte being combined with a specific ligand, said analyte either comprising at least one such chemical moiety or
2) in the case that said analyte lacks a redox catalyst property, said analyte is linked by said specific ligand to at least one such moiety or is linked by said specific ligand to a generator of at least one such moiety, said specific ligand being one member of either an antibody/antigen pair or a hybridization probe/target pair, and (b) at least one monomer capable of undergoing addition polymerization, said monomer being selected from the group consisting of acrylamide, N-octyl acrylamide, methacrylamide, N-methacrylamide, acrylic acid, methacrylic acid, hydroxymethyl acrylamide, methylene bisacrylamide, acrylonitrile, methyl acrylate, ethylene glycol methacrylate, propylene glycol methacrylate, acrylamide propane sulfonic acid, N-(3-aminopropyl)-methacrylamide, pentaerythritoltriacrylate, polyethyleneglycol diacrylate, vinyl pyrrolidine, vinyl pyridine, multivalent salts of acrylic acid, multivalent salts of methacrylic acid and combinations of the aforesaid monomers.

2. A composition according to claim 1, wherein the analyte is a redox catalyst moiety or a generator of a redox catalyst moiety.

3. A composition according to claim 1, which is a diagnostic immunoassay test composition wherein said specific ligand is selected from the group consisting of an antibody, an antigen binding segment of an antibody, an antigen and a hapten, wherein when the specific ligand is an antibody or an antigen binding segment of an antibody, the analyte is an antigen or a hapten and wherein when the specific ligand is an antigen or hapten, the analyte is an antibody or an antigen binding segment of an antibody.

4. A composition according to claim 1, which is a diagnostic test composition for the assay of a nucleic acid wherein said specific ligand is a hybridizable nucleic acid probe containing a known sequence, said sequence being single stranded and complementary to a single stranded segment of an analyte nucleic acid.

5. A composition according to claim 1, wherein the specific ligand for the analyte is linked to a chemical moiety which is a reductant.

6. A composition according to claim 1, wherein the reductant is a chelated metal.

7. A composition according to claim 6, wherein the chelated metal is selected from the group consisting of iron, copper, cobalt, manganese, nickel, silver, molybdenum and cerium.

8. A composition according to claim 1, wherein the specific ligand for the analyte is linked to a generator of a chemical moiety of the catalyst system.

9. A composition according to claim 8, wherein said generator generates an oxidant from a precursor.

10. A composition according to claim 9, wherein the generator of the oxidant is an oxidase enzyme that generates hydrogen peroxide.

11. A composition according to claim 10, wherein the oxidase enzyme is selected from the group consisting of lactate oxidase, glucose oxidase, L-gulonolactone oxidase, galactose oxidase, L-2-hydroxyacid oxidase, aldehyde oxidase, xanthine oxidase, dihydro-orotate dehydrogenase, D-aspartate oxidase, L-amino acid oxidase, D-amino acid oxidase, monamine oxidase, pyridoxaminephosphate oxidase, diamine oxidase, sarcosine oxidase, spermine oxidase, sulfite oxidase, hexose oxidase, L-sorbose oxidase, pyridoxol 4-oxidase, alcohol oxidase, tyramine oxidase, putrescine oxidase, 6-hydroxyl-L-nicotine oxidase, 6-hydroxy-D-nicotine oxidase, 2-aminophenol oxidase, superoxide dismutase and cytochrome oxidase.

12. A composition according to claim 8, wherein said generator generates a reductant from a precursor.

13. A composition according to claim 12, wherein the generator of the reductant is selected from the group consisting of a peroxidase enzyme, an oxidase enzyme and a dehydrogenase enzyme.

14. A composition according to claim 13, wherein the peroxidase enzyme is selected from the group consisting of horseradish peroxidase, myeloperoxidase, thyroid peroxidase, salivary peroxidase, intestinal peroxidase, lactoperoxidase and microperoxidase.

15. A composition according to claim 13, wherein the reductant for the peroxidase enzyme is selected from the group consisting of dihydroxyfumaric acid and acetylacetone.

16. A composition according to claim 13, wherein the oxidase enzyme is xanthine oxidase.

17. A composition according to claim 13, wherein the dehydrogenase enzyme is selected from the group consisting of glutathione reductase and ferredoxin-nicotinamide adenine dinucleotide phosphate reductase.

18. A composition according to claim 1, which further comprises an oxygen buffer.

19. A composition according to claim 18, wherein the oxygen buffer is selected from the group consisting of cobalt chelate and an oxygen oxidoreductase enzyme.

20. A composition according to claim 19, wherein the cobalt chelate is selected from the group consisting of the cobalt chelate of glycylglycine, histidine, diethylenetriamine, triethylenetetramine, and vitamin $B_{12a}$.

21. A composition according to claim 19, wherein the oxygen oxidoreductase is an oxidase enzyme.

22. A composition according to claim 21, wherein the oxidase enzyme is selected from the group consisting of alcohol oxidase, ascorbic acid oxidase, galactose oxidase, glucose oxidase, sarcosine oxidase, pyruvate oxidase, choline oxidase, amino acid oxidase and the xanthine oxidase.

* * * * *